United States Patent
Millet et al.

(10) Patent No.: US 10,980,724 B2
(45) Date of Patent: Apr. 20, 2021

(54) BICARBONATE-BASED AQUEOUS COSMETIC COMPOSITION

(71) Applicant: LABORATOIRES M&L, Manosque (FR)

(72) Inventors: Magali Millet, Les Mees (FR); Amandine Gadret, Manosque (FR)

(73) Assignee: LABORATOIRES M&L, Manosque (FR)

( * ) Notice: Subject to any disclaimer, the term of this patent is extended or adjusted under 35 U.S.C. 154(b) by 0 days.

(21) Appl. No.: 16/615,414

(22) PCT Filed: May 24, 2018

(86) PCT No.: PCT/FR2018/051229
§ 371 (c)(1),
(2) Date: Nov. 21, 2019

(87) PCT Pub. No.: WO2018/220314
PCT Pub. Date: Dec. 6, 2018

(65) Prior Publication Data
US 2020/0170908 A1    Jun. 4, 2020

(30) Foreign Application Priority Data
Jun. 2, 2017 (FR) ..................... 1754903

(51) Int. Cl.
| A61K 8/36 | (2006.01) |
| A61K 8/34 | (2006.01) |
| A61K 8/73 | (2006.01) |
| A61K 8/19 | (2006.01) |
| A61Q 15/00 | (2006.01) |

(52) U.S. Cl.
CPC ............... *A61K 8/36* (2013.01); *A61K 8/345* (2013.01); *A61K 8/731* (2013.01); *A61K 8/732* (2013.01); *A61Q 15/00* (2013.01); *A61K 2800/30* (2013.01); *A61K 2800/874* (2013.01)

(58) Field of Classification Search
CPC .... A61K 8/19; A61K 8/732; A61K 2800/874; A61K 8/731; A61K 8/36; A61Q 15/00
See application file for complete search history.

(56) References Cited

U.S. PATENT DOCUMENTS

| 4,534,962 A | 8/1985 | Marschner |
| 4,803,195 A * | 2/1989 | Holzner .................. A61K 8/11 512/4 |
| 5,302,373 A * | 4/1994 | Giacin .................... A61K 8/19 424/49 |
| 5,614,179 A | 3/1997 | Murphy et al. |
| 6,001,341 A * | 12/1999 | Genova .................... A61K 8/37 424/401 |
| 6,562,090 B1 * | 5/2003 | Melbouci ................. A61K 8/19 424/49 |
| 6,635,262 B2 * | 10/2003 | Jourdan ............... A45D 34/041 424/400 |
| 2005/0255064 A1 * | 11/2005 | Bruening ................. A61K 8/37 424/66 |
| 2009/0047226 A1 * | 2/2009 | Teckenbrock ......... A61K 8/732 424/59 |
| 2011/0256082 A1 * | 10/2011 | Klingman .............. A61K 8/365 424/65 |
| 2014/0271504 A1 * | 9/2014 | Hurkens ................. A61K 8/63 424/59 |
| 2018/0168954 A1 | 6/2018 | Millet et al. |

FOREIGN PATENT DOCUMENTS

| DE | 10 2015 223 837 | 9/2016 | |
| GB | 1553739 A * | 9/1979 | ............... A61K 8/19 |
| WO | WO 2016/185113 | 11/2016 | |

OTHER PUBLICATIONS

Deckner, G. "Natural-Based Thickeners." Prospector Knowledge Center (Mar. 4, 2016).*
Young, PM. "Sodium Starch Glycolate." Handbook of Pharmaceutical Excipients (2009) 663-666.*
Katzbauer, Barbara. "Properties and applications of xanthan gum." Polymer degradation and Stability 59.1-3 (1998): 81-84.*
Sanderson, George R. "Applications of xanthan gum." British polymer journal 13.2 (1981): 71-75.*
Written Opinion in International Application No. PCT/FR2018/051229, dated Sep. 24, 2018, pp. 1-6.

* cited by examiner

*Primary Examiner* — Bethany P Barham
*Assistant Examiner* — Peter Anthopolos
(74) *Attorney, Agent, or Firm* — Saliwanchik, Lloyd & Eisenschenk

(57) ABSTRACT

The present invention relates to an aqueous cosmetic composition based on a bicarbonate salt, said composition being stabilized by a pair of particular gelling agents, and also to the cosmetic use thereof as a deodorant. It also relates to a roll-on deodorant containing this composition.

12 Claims, No Drawings

BICARBONATE-BASED AQUEOUS COSMETIC COMPOSITION

CROSS-REFERENCE TO RELATED APPLICATION

This application is the U.S. national stage application of International Patent Application No. PCT/FR2018/051229, filed May 24, 2018.

SUBJECT OF THE INVENTION

The present invention relates to an aqueous cosmetic composition based on a bicarbonate salt, said composition being stabilized by a pair of particular gelling agents, and also to the cosmetic use thereof as a deodorant. The invention also relates to a roll-on deodorant containing this composition.

BACKGROUND OF THE INVENTION

Deodorants and antiperspirants have become indispensable hygiene products. While the first act on perspiration odors either by camouflaging them or by targeting the bacteria that feed on apocrine sweat, or else by absorbing perspiration, the second regulate the amount of sweat emitted. The innocuousness of the aluminum salts used as antiperspirant agents has been questioned over the past few years, and this has led to consumers turning to products containing natural deodorant agents, such as talc and/or certain plants in dried form or in the form of essential oils. However, the effectiveness of these products is not always optimal.

Sodium bicarbonate constitutes a recognized natural deodorant active agent. At the doses considered to be effective, its formulation is on the other hand complicated by its incompatibility with numerous starting materials. It in particular has a tendency to degrade in aqueous or aqueous-alcoholic solutions, in which it is moreover difficult to dissolve. In addition to the unpleasant feeling that it causes on the skin, the presence of sodium bicarbonate crystals is in particular problematic when this compound is introduced into compositions dispensed in roll-on deodorants, because of the propensity of these crystals to block the rollerball.

For this reason, roll-on deodorants contain a limited amount (less than 3% by weight) of sodium bicarbonate, or else it is recommended to shake them before use.

One solution for overcoming this problem is proposed in document U.S. Pat. No. 4,534,962. It consists in formulating the bicarbonate salts in an aqueous-alcoholic medium in the presence of a particular suspending agent, hydroxyethylcellulose, and optionally of polyols. It is indicated in this document that the other cellulose derivatives, and in particular carboxymethylcellulose, do not make it possible to prevent sodium bicarbonate sedimentation. It is moreover essential for the composition to contain large amounts of alcohol (at least 50%). The solution proposed is not therefore satisfactory, because of the irritation that the composition may cause on application, in particular to skin that has recently undergone hair removal.

An alternative solution is presented in document U.S. Pat. No. 5,614,179, which consists in coating bicarbonate crystallites with a mixture of fragrance and of polymer, generally by spraying. The polymer can be chosen from a diversity of materials of natural or synthetic origin, including plant gums, xanthan gum and cellulose derivatives. This process has the drawback of being complex and thus negatively affects the production costs of the deodorants for which it is implemented. In addition, the coated crystallites are intended to be incorporated into anhydrous compositions containing high volatile oil contents and not into aqueous gels or emulsions with a continuous aqueous phase, which are sought for the freshness effect that they provide.

SUMMARY OF THE INVENTION

After numerous research studies, the applicant has developed a combination of gelling agents which makes it possible to formulate bicarbonate salts in compositions with a continuous aqueous phase, while preventing the problems of sedimentation and/or crystallization of these salts. In addition, the bicarbonate salts are partly dissolved in water and partly in suspension in the composition, without negatively affecting the viscosity of the composition.

These compositions can in particular be used in the production of roll-on deodorants, that it is not necessary to shake before use. These compositions are thus easy to apply, effective against perspiration odors and capable of depositing on the skin a film with a smooth and fluid texture.

The subject of the invention is thus a cosmetic composition containing:
(a) from 3 to 10% by weight of at least one bicarbonate salt,
(b) xanthan gum,
(c) at least one optionally carboxymethylated glucose homopolymer, and
(d) from 40 to 95% by weight of water, the above percentages being expressed relative to the total weight of the composition.

Another subject of the invention is the cosmetic use of this composition for treating human body odor, in particular underarm odor.

Finally, the invention relates to a roll-on deodorant containing this composition.

DETAILED DESCRIPTION

The composition according to the invention is a composition containing from 40 to 95% by weight of water, preferably from 50 to 85% by weight of water and more preferentially from 60 to 80% by weight of water. It may be either an aqueous gel, or an oil-in-water emulsion. In any event, it is a composition with a continuous aqueous phase.

This composition comprises a bicarbonate salt, used as a deodorant agent. Said bicarbonate salt can represent from 3 to 10% by weight, and preferably from 4 to 6% by weight, based on the total weight of the composition. As bicarbonate salts, mention may be made of sodium, potassium, magnesium and ammonium salts, the sodium salt being preferred for use in this invention. According to one embodiment, the composition does not contain aluminum salts. On the other hand, it can however contain at least one additional deodorant active agent chosen from: bacteriostatic or bactericidal agents, such as chlorhexidine and salts thereof; triclosan; triclocarban; farnesol; essential oils of plant origin, chosen for example from essential oils of oregano, of palmarosa, of peppermint, of lavender, of lemon and of tea tree; plant extracts such as grapefruit seed extracts; zinc salts such as zinc gluconate, zinc pidolate and zinc ricinoleate; and mixtures thereof.

As indicated above, it has been observed that the composition according to the invention is stable in the presence of bicarbonate, in the sense that no crystallization and/or sedimentation of the bicarbonate is observed and that the texture of the composition remains fluid, without any notable variation in its viscosity over time. This effect is obtained by the addition of a combination of particular gelling agents, namely a xanthan gum and an optionally carboxymethylated glucose homopolymer, hereinafter referred to, for greater simplicity, as "glucose homopolymer".

The glucose homopolymer can be chosen from cellulose, such as microcrystalline cellulose, which is the colloidal crystalline fraction isolated from cellulose fibers; cellulose gum or carboxymethylcellulose gum; carboxymethylated starches; and mixtures thereof. It differs from glucose copolymers such as gellan gum. An example of a mixture of microcrystalline cellulose and carboxymethylcellulose, containing a predominant fraction by weight of microcrystalline cellulose, is the mixture available from the company FMC BioPolymer under the trade name Avicel® PC 611. The starches are preferably chosen from cornstarch, rice starch, tapioca starch or wheat starch. An example of carboxymethylated starch is that sold by the company J. Rettenmaier under the trade name Vivapharm® CS 152HV.

It is understood that the abovementioned glucose homopolymer is present as a constituent distinct from the bicarbonate salt, in the composition according to the invention, and that it does not constitute a coating of said salt. In general, it is preferable for the bicarbonate particles present in the composition according to the invention, in addition to the bicarbonate dissolved in water, not to be coated.

The glucose homopolymer can represent from 0.3 to 3% by weight and preferably from 0.3 to 1% by weight in the case of the carboxymethylated starch and from 1.2 to 2% by weight in the case of microcrystalline cellulose and cellulose gum, relative to the total weight of the composition.

For its part, the xanthan gum can represent from 0.1 to 2% by weight and preferably from 0.2 to 0.4% by weight, relative to the total weight of the composition.

In one embodiment, the composition according to the invention can also contain at least one additional aqueous-phase-gelling agent, in addition to the xanthan gum and the glucose homopolymer. This additional gelling agent can in particular be chosen from synthetic polymers, more particularly from acrylic polymers and preferentially from copolymers of (meth)acrylic acid and of $C_{10}$-$C_{30}$ alkyl (meth)acrylate. An example of such an amphiphilic copolymer is that sold by the company Lubrizol under the trade name Carbopol Ultrez® 20 Polymer.

The composition according to the invention advantageously does not contain surfactant within the meaning of the compounds listed in the McCutcheon dictionary "Emulsifiers & Detergents", 2017 edition.

It also preferably does not contain oil and thus constitutes an aqueous gel. However, as a variant, the composition according to the invention may contain at least one oil. In this case, it may or may not include a surfactant.

In the present description, the term "oil" is intended to mean a compound which is liquid at ambient temperature (25° C.) and atmospheric pressure ($10^5$ Pa) and which, when it is introduced in a proportion of at least 1% by weight in water at 25° C., is not at all soluble in water, or is soluble in an amount of less than 10% by weight, relative to the weight of oil introduced into the water. The oils may be volatile or nonvolatile. The term "nonvolatile oil" is intended to mean, in this description, an oil which remains on the skin at 25° C. and atmospheric pressure for at least one hour, in the absence of rubbing, and/or which has a vapor pressure of less than 0.001 mmHg under these conditions. The oils included in the composition according to the invention may or may not be volatile; they are advantageously nonvolatile.

As a variant, it may be a question of a mixture of nonvolatile oils (in the majority by weight) and volatile oils (in the minority by weight). Examples of volatile oils are in particular $C_{11}$ to $C_{14}$ linear alkanes and isoparaffins. In addition, the nonvolatile oils are preferably chosen from hydrocarbon-based oils, that is to say that they contain exclusively carbon, hydrogen and optionally oxygen atoms.

Examples of nonvolatile oils comprise:

esters of acids and of a monoalcohol, chosen from: mono- and polyesters of $C_2$-$C_{10}$ (preferably $C_6$-$C_{10}$) saturated linear acids and of $C_{10}$-$C_{18}$ (preferably $C_{10}$-$C_{14}$) saturated linear monoalcohols, mono- and polyesters of $C_{10}$-$C_{20}$ saturated linear acids and of $C_3$-$C_{20}$ (preferably $C_3$-$C_{10}$) branched or unsaturated monoalcohols; mono- and polyesters of $C_5$-$C_{20}$ branched or unsaturated acids and of $C_5$-$C_{20}$ branched or unsaturated monoalcohols; mono- and polyesters of $C_5$-$C_{20}$ unsaturated or branched acids and of $C_2$-$C_4$ linear monoalcohols;

$C_6$-$C_{12}$ fatty acid triglycerides, such as caprylic and capric acid triglycerides and triheptanoin;

$C_{10}$-$C_{20}$ branched and/or unsaturated fatty acids (such as linoleic acid, lauric acid and myristic acid);

$C_{10}$-$C_{20}$ branched and/or unsaturated fatty alcohols (such as octyldodecanol and oleyl alcohol);

hydrocarbons such as plant squalane extracted from olive oil;

dialkyl carbonates, such as dicaprylyl carbonate and diethylhexyl carbonate;

dialkyl ethers such as dicaprylyl ether; and mixtures thereof.

Mention may also be made of plant oils which contain one or more of the abovementioned constituents.

As esters of acids and of monoalcohols, mention may in particular be made of monoesters, such as the coco-caprylate/caprate mixture, ethyl macadamiate, shea butter ethyl ester, isostearyl isostearate, isononyl isononanoate, ethylhexyl isononanoate, hexyl neopentanoate, ethylhexyl neopentanoate, isostearyl neopentanoate, isodecyl neopentanoate, isopropyl myristate, octyldodecyl myristate, isopropyl palmitate, ethylhexyl palmitate, hexyl laurate, isoamyl laurate, cetostearyl nonanoate, propylheptyl caprylate, and mixtures thereof. Other esters that can be used are diesters of acids and of monoalcohols, such as diisopropyl adipate, diethylhexyl adipate, diisopropyl sebacate and diisoamyl sebacate.

Examples of plant oils are in particular wheatgerm oil, sunflower oil, argan oil, hibiscus oil, coriander oil, grapeseed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, rapeseed oil, blackcurrant oil, evening primrose oil, lavender oil, borage oil, millet oil, barley oil, quinoa oil, rye oil, safflower oil, candlenut oil, passionflower oil, rose musk oil or camellia oil.

In addition to the above oils, the composition according to the invention may also contain at least one plant butter. The term "plant butter" is intended to mean a pasty fatty substance with a reversible liquid/solid change of state, having, in the solid state, an anisotropic crystal organization and comprising, at a temperature of 23° C., a liquid fraction and a solid fraction. Examples of plant butters are shea butter, cocoa butter and mango butter, and mixtures thereof.

In one preferred embodiment of the invention, the composition also contains at least one polyol, such as glycerol, propylene glycol (propane-1,2-diol), dipropylene glycol, propane-1,3-diol, butane-1,2-diol, butane-1,4-diol, butane-2,3-diol, butane-1,3-diol, pentane-1,5-diol, pentane-1,2-diol, hexane-1,6-diol, octane-1,8-diol, 2-methylpentane-2,4-diol, methylpropanediol, isopentyldiol or a mixture thereof. Glycols such as propylene glycol are particularly preferred. The polyol may represent from 10 to 50% by weight, preferably from 20 to 30% by weight, relative to the total weight of the composition.

Moreover, the composition preferably contains no monoalcohol, in particular no ethanol.

Other optional constituents that may be included in the composition according to the invention are pulverulent fillers, which are suitable for absorbing moisture and sweat and which are generally in the form of porous or hollow microparticles, preferably porous microparticles. These microparticles are in principle substantially spherical. These fillers can in particular be chosen from:
- organic fillers such as: powders of polysaccharides and in particular of starch, such as corn, rice, tapioca or wheat starch; powders of acrylic polymers such as poly(methyl methacrylate), of polyamides or of polyolefins; powders of dried algae such as *Corallina officinalis*;
- inorganic fillers such as silica, clays, perlite and talc;
- and mixtures thereof.

These fillers can represent from 2 to 20% by weight, and preferably from 2 to 5% by weight, relative to the total weight of the composition.

The composition according to the invention may also comprise additives chosen in particular from fragrances, antioxidants, such as tocopherol, dyes, preserving agents, and mixtures thereof.

The pH of the composition is advantageously between 7.5 and 9 and can be adjusted by adding an organic acid such as citric acid.

The composition according to the invention is in the form of a gel or a cream, the viscosity of which is advantageously between 1500 and 4000 centipoises, as measured using a Brookfield® rheometer equipped with an LV3 spindle (set to speed 12) at 20° C.

It can be used as a deodorant product, in particular in a roll-on deodorant.

EXAMPLES

The invention will be understood more clearly in the light of the following examples, which are given purely by way of illustration and are not intended to limit the scope of the invention, defined by the appended claims.

Example 1: Aqueous Gel

A gel is prepared by mixing the following ingredients, in the weight proportions indicated below.

| | |
|---|---|
| SODIUM BICARBONATE | 5% |
| MICROCRISTALLINE CELLULOSE & CELLULOSE GUM | 1-2% |
| XANTHAN GUM | 0.2-1% |
| PROPYLENE GLYCOL | 20% |
| CITRIC ACID | qs |
| Acrylic gelling agent | 0.1-0.5% |
| Fragrance(s) | qs |
| Preserving agent(s) | qs |
| Water | qs 100% |

This gel was prepared in the following way: the combination of gelling agents according to the invention and the propylene glycol were successively mixed with the acrylic gelling agent dispersed beforehand in water at 80° C., then the temperature was decreased to 50° C. and the sodium bicarbonate was introduced, followed by the preserving agents. The temperature was further reduced to 38° C. before adding the fragrances.

This composition was poured, at ambient temperature, into a bottle with a dispensing rollerball.

Sensory analysis: this composition was tested for 1 week by a panel of 20 volunteers, 70% of whom liked its effectiveness and 85% of whom judged its texture to be pleasant.

Example 2: Emulsion

A fluid emulsion was prepared by mixing the following ingredients, in the weight proportions indicated below.

| | |
|---|---|
| SODIUM BICARBONATE | 5% |
| MICROCRISTALLINE CELLULOSE & CELLULOSE GUM | 1-2% |
| XANTHAN GUM | 0.2-1% |
| PROPYLENE GLYCOL | 20% |
| CAPRYLIC/CAPRIC TRIGLYCERIDE | 5% |
| Acrylic gelling agent | 0.1-0.5% |
| CITRIC ACID | qs |
| Preserving agent(s) | qs |
| Water | qs 100% |

Example 3: Stability Test

Four samples A to D of the compositions of examples 1 and 2 were taken, and were dispensed into four pill bottles stored respectively at 4° C., 25° C., 40° C. and 50° C. The stability of samples 1A to 1C and 2A to 2C is evaluated each week for 1 month, then every 15 days for 3 months, and the stability of samples 1D and 2D is evaluated each week for 1 month.

The appearance of the samples tested was observed. The results are presented in table 1 below:

TABLE 1

| Product tested | After 3 months at 4° C. | After 3 months at 25° C. | After 3 months at 40° C. | After 1 month at 50° C. |
|---|---|---|---|---|
| Example 1 | stable | stable | stable | stable |
| Example 2 | stable | stable | stable | stable |

It emerges from this test that the products according to the invention are stable at 40° C. for 3 months and at 50° C. for 1 month, that is to say under accelerated aging conditions which are considered to be representative of the behavior of the product stored for three years under normal storage conditions.

Example 4: Comparative Example

The stability of several compositions similar to that of example 1 was evaluated, while replacing the xanthan gum:
- either with gellan gum (Ex. A), which is a heteropolysaccharide made up of monomers of D-glucose, L-rhamnose and D-glucuronic acid (Kelcogel® CG-HA from CP Kelco),
- or with a carbomer (Ex. B), that is to say a homopolymer of acrylic acid (Carbopol Ultrez® 30 from Lubrizol),
- or with a carboxymethylated starch (Ex. C) (Vivapharm® CS 152HV from J. Rettenmaier).

Similar formulas were prepared, which either did not contain propylene glycol (respectively Ex. 1-1, A-1, B-1 and C-1), or contained 30% of propylene glycol instead of 20% (respectively Ex. 1-2 and C-2), and they were tested under the same conditions.

These compositions were subjected to the same aging protocol as that described above and were then evaluated with the naked eye and optionally observed under a microscope in order to verify the presence or absence of bicarbonate sedimentation.

The results of these tests are collated in table 2 below.

TABLE 2

| Product tested | Observations |
| --- | --- |
| Ex. 1 | Stable |
| Ex. 1-1 | Stable |
| Ex. 1-2 | Stable |
| Ex. A | Gelatinous, phase separation at 50° C. |
| Ex. A-1 | Gelatinous |
| Ex. B | Gelatinous with release |
| Ex. B-1 | Gelatinous with release |
| Ex. C | Stable |
| Ex. C-1 | Stable |
| Ex. C-2 | Stable |

In the case of the comparative products, a syneresis phenomenon, resulting in the presence of a water-covered gel phase, was observed.

The invention claimed is:

1. A roll-on deodorant comprising a cosmetic composition containing
   (a) from 3 to 10% by weight of at least one bicarbonate salt,
   (b) xanthan gum,
   (c) at least one carboxymethylated glucose homopolymer,
   (d) from 40 to 95% by weight of water, and
   (e) from 10 to 50% by weight of polyol,
   the above percentages being expressed relative to the total weight of the composition,
   wherein the composition is free of ethanol.

2. The roll-on deodorant as claimed in claim 1, wherein the bicarbonate salt represents from 4 to 6% by weight, relative to the total weight of the composition.

3. The roll-on deodorant as claimed in claim 1, wherein the carboxymethylated glucose homopolymer is selected from carboxymethylcellulose, carboxymethylated starch, and mixtures thereof.

4. The roll-on deodorant as claimed in claim 1, wherein the composition contains a mixture of cellulose and carboxymethylcellulose.

5. The roll-on deodorant as claimed in claim 1, wherein the composition contains a carboxymethylated starch.

6. The roll-on deodorant as claimed in claim 1, wherein the composition is free of oil.

7. The roll-on deodorant as claimed in claim 1, wherein the composition contains from 50 to 85% by weight of water.

8. The roll-on deodorant as claimed in claim 1, wherein said polyol is glycerol, propylene glycol (propane-1,2-diol), dipropylene glycol, propane-1,3-diol, butane-1,2-diol, butane-1,4-diol, butane-2,3-diol, butane-1,3-diol, pentane-1,5-diol, pentane-1,2-diol, hexane-1,6-diol, octane-1,8-diol, 2-methylpentane-2,4-diol, methylpropanediol, isopentyldiol or a mixture thereof.

9. The roll-on deodorant as claimed in claim 1, wherein said polyol is propylene glycol.

10. The roll-on deodorant as claimed in claim 1, which comprises from 20 to 30% by weight of polyol.

11. A method of treating human body odor comprising administering the roll-on deodorant as claimed in claim 1 to a human.

12. The method as claimed in claim 11, wherein the human body odor is armpit odor and the roll-on deodorant is applied to the armpit of said human.

* * * * *